United States Patent
Figg et al.

(10) Patent No.: US 10,025,086 B2
(45) Date of Patent: *Jul. 17, 2018

(54) METHOD OF AND APPARATUS FOR ANALYSIS OF A SAMPLE OF BIOLOGICAL TISSUE CELLS

(71) Applicant: Solentim Limited, Dorset (GB)

(72) Inventors: Aaron Figg, Ringwood (GB); David Elverd, Bournemouth (GB)

(73) Assignee: SOLENTIM LIMITED, Dorset (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/438,360

(22) Filed: Feb. 21, 2017

(65) Prior Publication Data

US 2017/0160536 A1    Jun. 8, 2017

Related U.S. Application Data

(63) Continuation of application No. 14/351,320, filed as application No. PCT/GB2012/052498 on Oct. 9, 2012, now Pat. No. 9,600,710.

(30) Foreign Application Priority Data

Oct. 14, 2011    (GB) .................................. 1117739.1

(51) Int. Cl.
   *G02B 21/36*    (2006.01)
   *G02B 21/24*    (2006.01)
   (Continued)

(52) U.S. Cl.
   CPC ......... *G02B 21/367* (2013.01); *G01N 21/253* (2013.01); *G02B 21/0064* (2013.01);
   (Continued)

(58) Field of Classification Search
   CPC combination set(s) only.
   See application file for complete search history.

(56) References Cited

U.S. PATENT DOCUMENTS

| 4,207,554 A | 6/1980 | Resnick et al. |
| 5,604,344 A * | 2/1997 | Finarov ................ G02B 21/244 |
| | | 250/201.3 |

(Continued)

FOREIGN PATENT DOCUMENTS

| EP | 1 324 097 A2 | 7/2003 | |
| EP | 1324097 A2 * | 7/2003 | ........... G02B 21/367 |

(Continued)

OTHER PUBLICATIONS

Patents Act 1977: Examination Report under Section 18(3) for Great Britain Application No. 1117739.1, dated Jun. 22, 2016, 4 pages.

(Continued)

*Primary Examiner* — Tsung-Yin Tsai

(74) *Attorney, Agent, or Firm* — Westman, Champlin & Koehler, P.A.

(57) ABSTRACT

At least first and second digital images of the sample are acquired having different focal heights relative to a platform on which the cells are disposed. A contrast matrix is produced having elements computed in dependence upon the difference between the values of the corresponding pixels in the first and second images. A phase matrix is produced by convolution of the contrast matrix with a predetermined distance matrix. The phase matrix is used to assess characteristics of the sample, such as the presence of cells in the sample or the heights of cells in the sample.

20 Claims, 9 Drawing Sheets

(51) Int. Cl.
*G02B 21/00* (2006.01)
*G02B 21/14* (2006.01)
*G01N 21/25* (2006.01)
*G06K 9/00* (2006.01)
*G06T 7/00* (2017.01)

(52) U.S. Cl.
CPC ........... *G02B 21/14* (2013.01); *G02B 21/244* (2013.01); *G06K 9/0014* (2013.01); *G06K 9/00134* (2013.01); *G06T 7/0012* (2013.01); *G06T 2207/10024* (2013.01); *G06T 2207/10056* (2013.01); *G06T 2207/10152* (2013.01); *G06T 2207/20021* (2013.01); *G06T 2207/20221* (2013.01); *G06T 2207/30024* (2013.01)

(56) References Cited

U.S. PATENT DOCUMENTS

| | | | | |
|---|---|---|---|---|
| 6,021,223 | A * | 2/2000 | Toyoda | G02B 27/46 359/237 |
| 7,039,553 | B2 | 5/2006 | Nugent et al. | |
| 2001/0038680 | A1 * | 11/2001 | Davidson | A61B 6/484 378/43 |
| 2003/0199752 | A1 * | 10/2003 | Sakaida | A61B 6/00 600/410 |
| 2005/0121596 | A1 * | 6/2005 | Kam | G01N 21/6458 250/201.2 |
| 2005/0168808 | A1 * | 8/2005 | Ishiwata | G02B 21/14 359/368 |
| 2008/0187208 | A1 * | 8/2008 | Shirota | G06K 9/00134 382/133 |
| 2009/0166558 | A1 * | 7/2009 | Nagayama | H01J 37/04 250/442.11 |
| 2009/0168155 | A1 * | 7/2009 | Matsui | G02B 21/14 359/368 |
| 2010/0075373 | A1 * | 3/2010 | Hoyt | G01N 1/30 435/40.5 |
| 2010/0172020 | A1 * | 7/2010 | Price | G02B 21/0016 359/381 |
| 2014/0056505 | A1 * | 2/2014 | Hoyt | G06K 9/00127 382/133 |
| 2014/0247974 | A1 | 9/2014 | Figg et al. | |

FOREIGN PATENT DOCUMENTS

| | | | | |
|---|---|---|---|---|
| GB | 201117739 | * | 11/2011 | ........... G02B 21/367 |
| GB | 2495537 | A | 4/2013 | |
| WO | 2007/131602 | A1 | 11/2007 | |
| WO | 2011/049608 | A2 | 4/2011 | |
| WO | 2013/054100 | A2 | 4/2013 | |

OTHER PUBLICATIONS

International Search Report and Written Opinion for PCT Application No. PCT/GB2012/052498, dated May 6, 2013, 19 pages.
Additional Search Reports under Patents Act 1977: Search Report under Section 17(6) for Great Britain Application No. 1117739.1, dated Dec. 22, 2014, 6 pages.
Teague, Michael Reed; "Deterministic phase retrieval: a Green's function solution"; J. Opt. Soc. Am./vol. 73, No. 11/Nov. 1983, 0030-3941/83/111434-08$01.00, 8 pages.
Patents Act 1977: Combined Search and Examination Report under Sections 17 and 18(3) for Great Britain Patent Application No. 1613925.5, dated Jan. 20, 2017, 6 pages.
Patents Act 1977: Combined Search and Examination Report under Sections 17 and 18(3) for Great Britain Patent Application No. 1613932.1, dated Jan. 20, 2017, 6 pages.
USPTO mailings from prosecution for U.S. Appl. No. 14/351,320, filed Apr. 11, 2014, including: Non-Final Rejection dated Jan. 6, 2016, 13 pages; Final Rejection dated Apr. 25, 2016, 16 pages; Non-Final Rejection dated Aug. 11, 2016, 11 pages; and Notice of Allowance dated Nov. 8, 2016, 9 pages; 49 total pages.

* cited by examiner

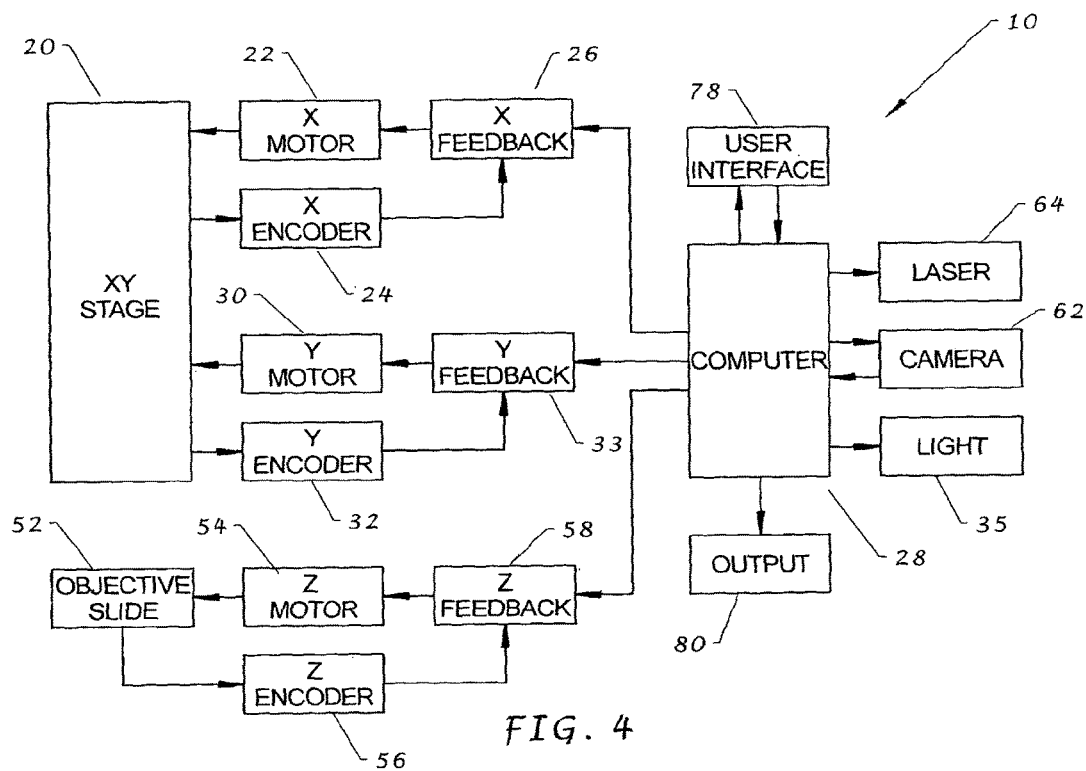
FIG. 4
FIG. 5
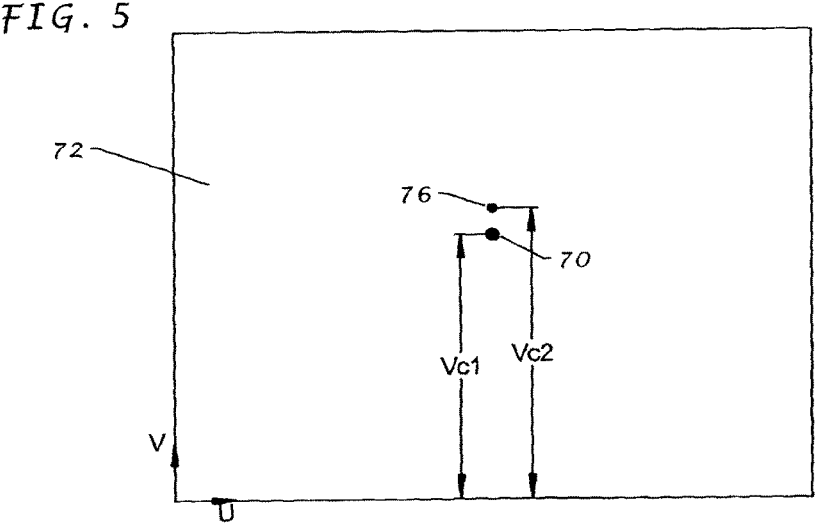

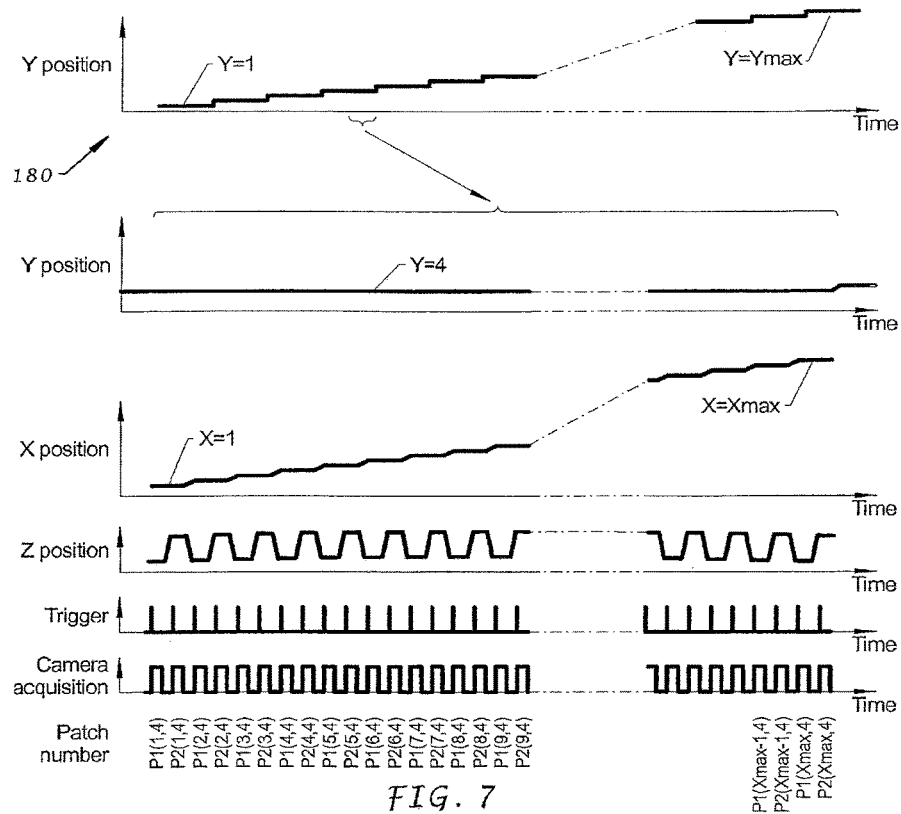
FIG. 7
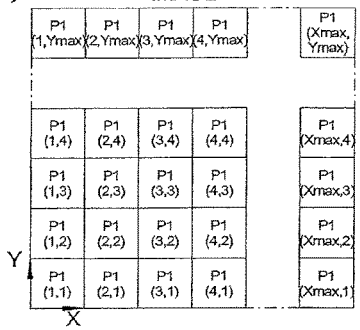
FIG. 8A  IMAGE I₁
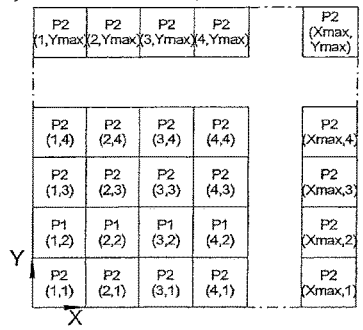
FIG. 8B  IMAGE I₂

METHOD OF AND APPARATUS FOR ANALYSIS OF A SAMPLE OF BIOLOGICAL TISSUE CELLS

CROSS-REFERENCE TO RELATED APPLICATIONS

This Application is a continuation of U.S. application Ser. No. 14/351,320, filed on 11 Apr. 2014, which is a Section 371 National Stage Application of International Application No. PCT/GB2012/052498, filed 9 Oct. 2012 and published as WO 2013/054100 A2 on 18 Apr. 2013, in English, the contents of which are hereby incorporated by reference in their entirety.

DESCRIPTION

This invention relates to a method of and apparatus for analysis of a sample of biological tissue cells. The invention is particularly, but not exclusively, applicable to the non-destructive analysis of living and/or dead cells to measure the proliferation and viability of the cells in a tissue culture sample.

Cells are often transparent and invisible or barely visible. They can be stained to render them more clearly visible so that they can be counted. However, staining cells may influence the cells and the result of the study. Furthermore, manually counting the cells in a cell culture vessel is tedious, time consuming and costly.

Thus, there is a need for a method for analyzing samples in a non-destructive manner. Hence, an improved method and device would be advantageous and in particular a non-destructive method allowing for increased flexibility and which is less time consuming.

When radiation, such as a beam of light, passes through a cell in a culture medium having a different refractive index to the cell, there is a phase change which depends on the relative refractive index of the cell and the thickness of the cell. The phase change can be measured and quantified by using an interferometer. However, non-interferometric techniques may also be used to provide phase information with the benefit of being easy to implement by solving the transport of intensity equation (TIE). This equation is described in "Deterministic Phase Retrieval: A Green's Function Solution", M. R. Teague, J. Opt. Soc. Am. 73 1434-1441 (1983).

U.S. Pat. No. 7,039,553 describes an approach to solving the TIE. By working in the frequency domain, using Fourier transform and inverse Fourier transform, the TIE equation is solved and the phase information is determined. A disadvantage of this approach is that, although the Fourier transform is easy to implement, it is prone to the background noise in the digital image. U.S. Pat. No. 7,039,553 therefore introduces a filter which involves a noise related arbitrary coefficient to address this issue. But once this coefficient is set to non-zero, the phase derived information is no longer accurate.

The present invention, or at least specific embodiments of it, seeks to derive accurate phase information in a simple manner.

The invention results from a realization that two simplifications can be applied to the TIE when working with typical tissue cells, and that by working in the spatial domain, rather than the frequency domain, the phase information can be simply deduced.

In accordance with a first aspect of the present invention, there is provided a method of analysis of a sample of biological tissue cells disposed on a platform, the method comprising the steps of: acquiring at least first and second images of the sample, the images having different focal heights relative to the platform, and each of the acquired images comprising a matrix of pixels; computing a contrast matrix having elements corresponding to the pixels in the acquired images, the value of each element of the contrast matrix being computed in dependence upon the difference between the values of the corresponding pixels in the first and second images; computing a phase matrix having elements corresponding to the elements in the contrast matrix, the phase matrix being a convolution of the contrast matrix and a predetermined distance matrix; and using the phase matrix to assess characteristics of the sample.

Although the method of the invention does not preclude the use of more than two images, two images are sufficient. By contrast, in the method described in U.S. Pat. No. 7,039,553, it is necessary to acquire at least three images of the sample.

Preferably, each element of the contrast matrix is computed so that its value is also dependent on the sum of the values of the corresponding pixels in the first and second images, and in particular each element of the contrast matrix is preferably computed so that its value is substantially proportional to the difference between the values of the corresponding pixels in the first and second images divided by the sum of those values.

Preferably, each element of the phase matrix is computed so that its value is substantially proportional to a weighted average of the values of a respective predetermined set of elements in the contrast matrix neighboring that one of the elements in the contrast matrix corresponding to the respective element of the phase matrix. In particular, in computing the weighted average, each weighting may be substantially inversely proportional to the spacing between the respective element and that one of the elements in the contrast matrix corresponding to the respective element of the phase matrix.

Each element of the phase matrix is preferably also computed so that its value is substantially proportional to the difference in focal heights of the first and second acquired images.

In the case where the sample and the platform are substantially transparent, the acquired images are preferably produced from light passing through the platform and the sample.

An optical system employed in the method of the first aspect of the invention may include a camera for acquiring the images, and an objective optical element disposed on an optical axis between the camera and the platform.

The step of acquiring each of the first and second images preferably comprises the steps of acquiring a set of image patches of an array of respective portions of the sample, and stitching the image patches together to form the respective image. Although the image patches may be of non-overlapping patches of the sample, the image patches for each of the first and second images are preferably of overlapping portions of the sample, and, in the step of stitching together the image patches, the patches are blended together in the areas of overlap. The set of image patches for the second image is preferably staggered, in the plane of the images, with respect to the set of image patches for the first image. The image patches are preferably acquired alternately for the first and second images.

The method of the first aspect of the invention may include the step of scanning the platform and the optical system relative to each other, and in this case at least some of the image patches are preferably acquired while the platform and optical system are moving relative to each other, with the sample being illuminated by a flashing light source synchronized with movement of the platform and optical system relative to each other. In the case where the camera is responsive to a trigger signal to commence, after a delay, acquisition of such an image patch provided that the camera is not already acquiring an image patch, and the lightsource is responsive to a trigger signal to produce a flash of light, common trigger signals are preferably provided in pairs to both the camera and the light source so that the first trigger signal of each pair triggers the camera and the light source, and the second trigger signal of each pair triggers the light source while the camera is acquiring an image patch.

The method of the first aspect of the invention preferably includes the steps of determining a measure of the height of the platform on which each portion of the sample is disposed; and adjusting the focal heights of the image patches in dependence upon the respective measures of the height of the platform. In this case, the focal heights of the image patches are preferably adjusted by moving the objective optical element. The measure of the height of the platform is preferably determined by projecting a beam of light at the platform at an inclined angle to the platform so that the beam is reflected, and detecting the reflected beam. More particularly, the beam of light is preferably projected into the objective optical element substantially parallel to and offset from the optical axis so that the beam is projected from the objective optical element to the platform at said inclined angle; whereupon the reflected beam is projected back into the objective optical element so that the reflected beam is projected from the objective optical element to the camera; and the reflected beam is detected by the camera.

In the case where the first-mentioned reflected beam is reflected by an under surface of the platform, and a second beam is reflected by an upper surface of the platform and is projected back into the objective optical element so that the second reflected beam is also projected from the objective optical element to the camera; the method of the first aspect of the invention preferably further includes the step of choosing whether to determine the measure of the height of the platform on which each portion of the sample is disposed from the first reflected beam or the second reflected beam.

The step of acquiring at least one of the first and second images may include the steps of: illuminating the sample with light of a first color and while doing so acquiring a first grey scale image component of the sample; subsequently illuminating the sample with light of a second different color and while doing so acquiring a second grey scale image component of the sample; and combining the first and second image components to produce a color image. This enables a color image to be produced despite employing either a monochrome or color camera. The method may further include the steps of: illuminating the sample with light of a third different color and while doing so acquiring a third grey scale image component of the sample; and combining the third image components with the first and second image components to produce the color image. In this way, a full color image may be produced, for example by illuminating the sample with red, green and blue light.

Some of these features of the first aspect of the invention may be provided independently of others of those features. Therefore in accordance with a second aspect of the present invention there is provided a method of analysis of a sample of biological tissue cells disposed on a platform, the method comprising the steps of: acquiring, using an optical system including a camera, a set of image patches of an array of respective portions of the sample; stitching the image patches together to form an image of the sample; and using the image to assess characteristics of the sample; wherein at least some of the image patches are acquired while the platform and optical system are moving relative to each other; and the sample is illuminated by a flashing light source synchronized with movement of the platform and optical system relative to each other.

Furthermore, in accordance with a third aspect of the present invention, there is provided a method of analysis of a sample of biological tissue cells disposed on a platform, the method comprising the steps of: notionally dividing the sample up into an array of portions; determining a measure of the height of the platform on which each portion of the sample is disposed; acquiring, using an optical system including a camera and an objective optical element disposed between the camera and the platform, a set of image patches of the portions of the sample with the focal height of each image patch being adjusted in dependence upon the respective measure of the height of the platform; stitching the image patches together to form an image of the sample; using the image to assess characteristics of the sample; wherein the measure of the height of the platform is determined by projecting a beam of light into the objective optical element substantially parallel to and offset from the optical axis so that the beam is projected from the objective optical element to the platform at an inclined angle to the platform so that the beam is reflected, and the reflected beam is projected back into the objective optical element so that the reflected beam is projected from the objective optical element to the camera; using the camera to acquire an image of the reflected beam; and detecting the position of the reflected beam in the image.

Moreover, in accordance with a fourth aspect of the invention, there is provided a method of analysis of a sample of biological tissue cells disposed on a platform, the method comprising the steps of: illuminating the sample with light of a first color and while doing so acquiring a first grey scale image component of the sample; subsequently illuminating the sample with light of a second different color and while doing so acquiring a second grey scale image component of the sample; combining the first and second image components to produce a color image; and using the color image to assess characteristics of the sample.

A fifth aspect of the invention extends to an apparatus for analysis of a sample of biological tissue cells, the apparatus comprising means for performing the steps of a method according to the first, second, third or fourth aspect of the invention. In particular, said means preferably includes: an optical system including a camera and an objective optical element; a platform on which the sample of biological tissue cells can be disposed; a motor system for moving the platform and the objective optical element relative to each other in three orthogonal directions; and a controller for causing the optical system and motor system to perform the steps of a method according to the first, second, third or fourth aspect of the invention. The controller preferably includes a programmable computer. A sixth aspect of the invention extends to computer program per se for programming the computer of an apparatus according to the fifth aspect of the invention so that the apparatus performs a method according to the first, second, third or fourth aspect of the invention.

In accordance with a seventh aspect of the invention, there is provided a computer program for use with a computer in the analysis of a sample of biological tissue cells disposed on a platform. The program comprises instructions for causing the computer to: take at least first and second image matrices of values of pixels representing images of the sample having different focal heights relative to the platform; compute a contrast matrix having elements corresponding to the pixels in the image matrices, the value of each element of the contrast matrix being computed in dependence upon the difference between the values of the corresponding pixels in the first and second image matrices; and compute a phase matrix having elements corresponding to the elements in the contrast matrix, the phase matrix being a convolution of the contrast matrix and a predetermined distance matrix. The program may further comprise an instruction for causing the computer to compute an assessment of characteristics of the sample from the phase matrix.

In accordance with an eighth aspect of the invention, there is provided medium storing a computer program according to the seventh aspect of the invention.

A specific embodiment of the present invention will now be described, purely by way of example, with reference to the accompanying drawings, in which:

FIG. 4 is a block diagram of electrical components of the analysis apparatus;

FIG. 5 is an example of an image acquired by a camera of the apparatus;

Figure 9:
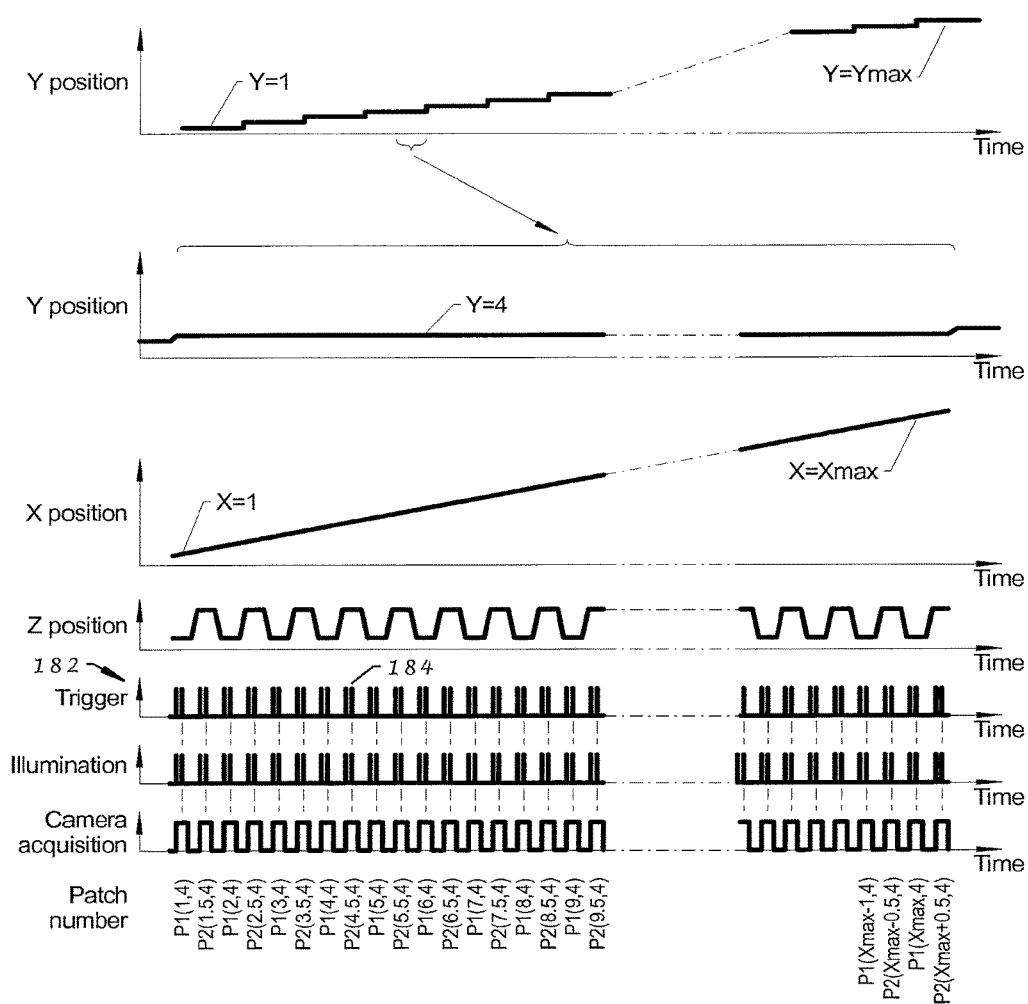

FIGS. 6A-D are flow diagrams of the operation of the apparatus;

FIG. 7 is a timing diagram for the apparatus;

FIGS. 8A-B illustrate patches of two images produced when the timing of FIG. 7 is employed;

FIG. 9 is a modified timing diagram for the apparatus; and

Figure 10A:
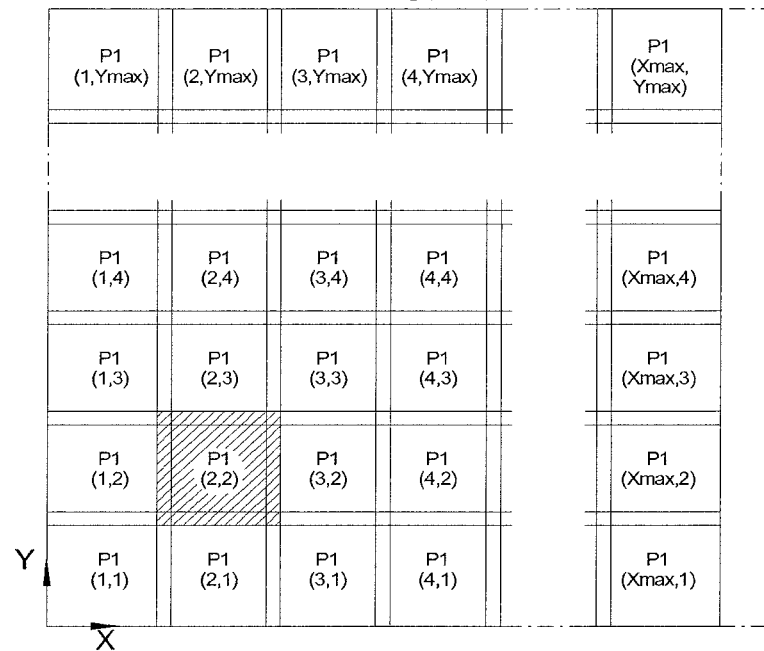
Figure 10B:
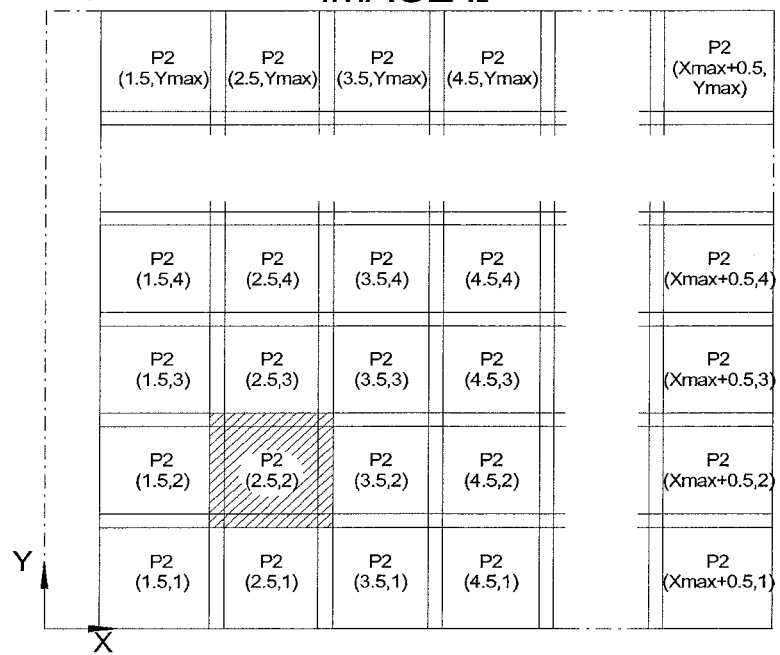

FIGS. 10A-B illustrate patches of two images produced when the timing of FIG. 9 is employed.

As mentioned above, the invention results from a realization that two simplifications can be applied to the TIE when working with typical tissue cells, and that by working in the spatial domain, rather than the frequency domain, the phase information can be simply deduced. Consider a central focal plane at a particular position along a Z axis, and consider a pair of parallel focal planes equispaced a distance of $\Delta f$ to either side of the central focal plane. Digital images h, $I_1$, $I_2$ are acquired of each of the focal planes. For a phase target, an image $I_0$ of the central plane is simply the pixel-by-pixel mean of the acquired images, $I_0=(I_1+I_2)/2$. A contrast matrix C can be calculated on a pixel-by-pixel basis such that $C=(I_1-I_2)/I_0$. The TIE equation for the wave field is $$\nabla_\perp \times [I \times (\nabla_\perp \phi)] = -k \times \frac{\partial I}{\partial z},$$

where: I is the intensity in the plane; the gradient operator in the place is denoted $\nabla_\perp$; k is the wave number of the radiation;

$$\frac{\partial I}{\partial z}$$

is the intensity derivative or the rate of change of intensity; $\phi$ is the phase; and z is the direction in which the light wave travels.

Two assumptions can be made about the object being images, namely: (1) it is a "thin phase object" meaning that light can pass through it and has its phase changed only slightly; and (2) its density is not too high. With these assumptions, the TIE equation is simplified from $$\nabla_\perp \times [I \times (\nabla_\perp \phi)] = -k \times \frac{\partial I}{\partial z} \text{ to } \nabla^2 \phi = \frac{k}{2\Delta f} \times C,$$

in which $\phi$ can be expressed as $$\phi = -\frac{q \times \Delta D}{4\lambda \times \Delta f} \times (C \otimes N)$$

where: q is the pixel size for the optical system, $\Delta D$ is the depth of field for the optical system; $\lambda$ is the typical wavelength of the optical system; $(C \otimes N)$ is the 2-D convolution of the contrast matrix C and a distance index matrix N.

Figure 1:
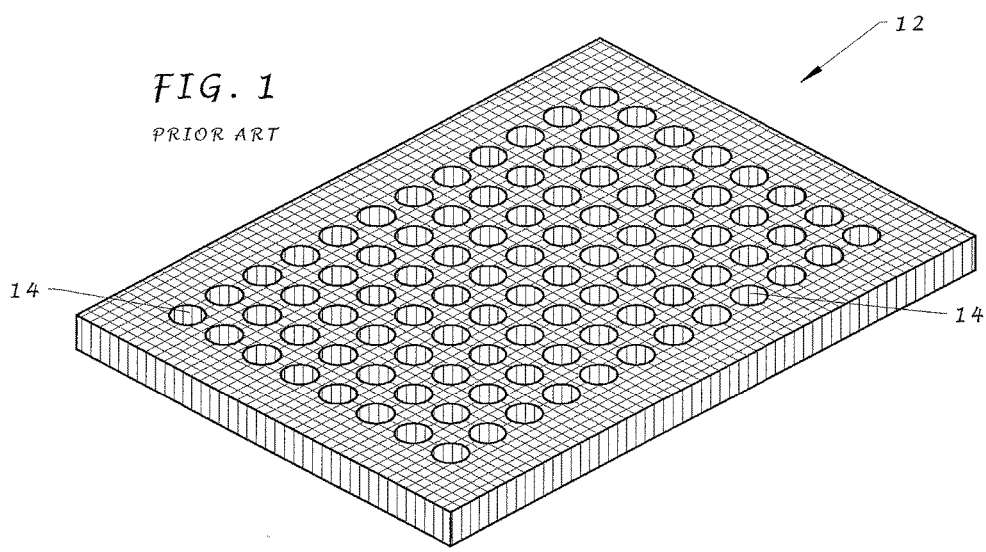
FIG. 1 is an isometric view of a known microwell container that may be used for containing specimens to be analyzed.
Figure 2:
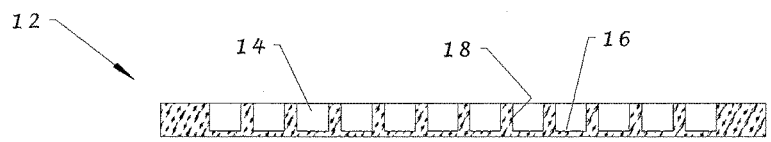
FIG. 2 is a sectioned side view of the microwell container.

Referring to FIGS. 1 and 2 of the drawings, in the analysis apparatus of the embodiment of the invention, specimens to be analyzed together with a liquid culture medium are placed in a microwell container 12 of known design. The container 12 is molded from transparent plastics material and has a rectangular array of compartments 14. Each compartment 14 has a floor (or platform) 16 and a cylindrical side wall 18. Although the underside of the floors 16 of the compartments 14 is approximately planar, it may deviate from a perfect plane due to distortion introduced during cooling of the plastics material during the molding process. The floors 16 are of substantially uniform thickness, and the top surfaces of the floors 16 may also not lie in a common plane.

Figure 3:
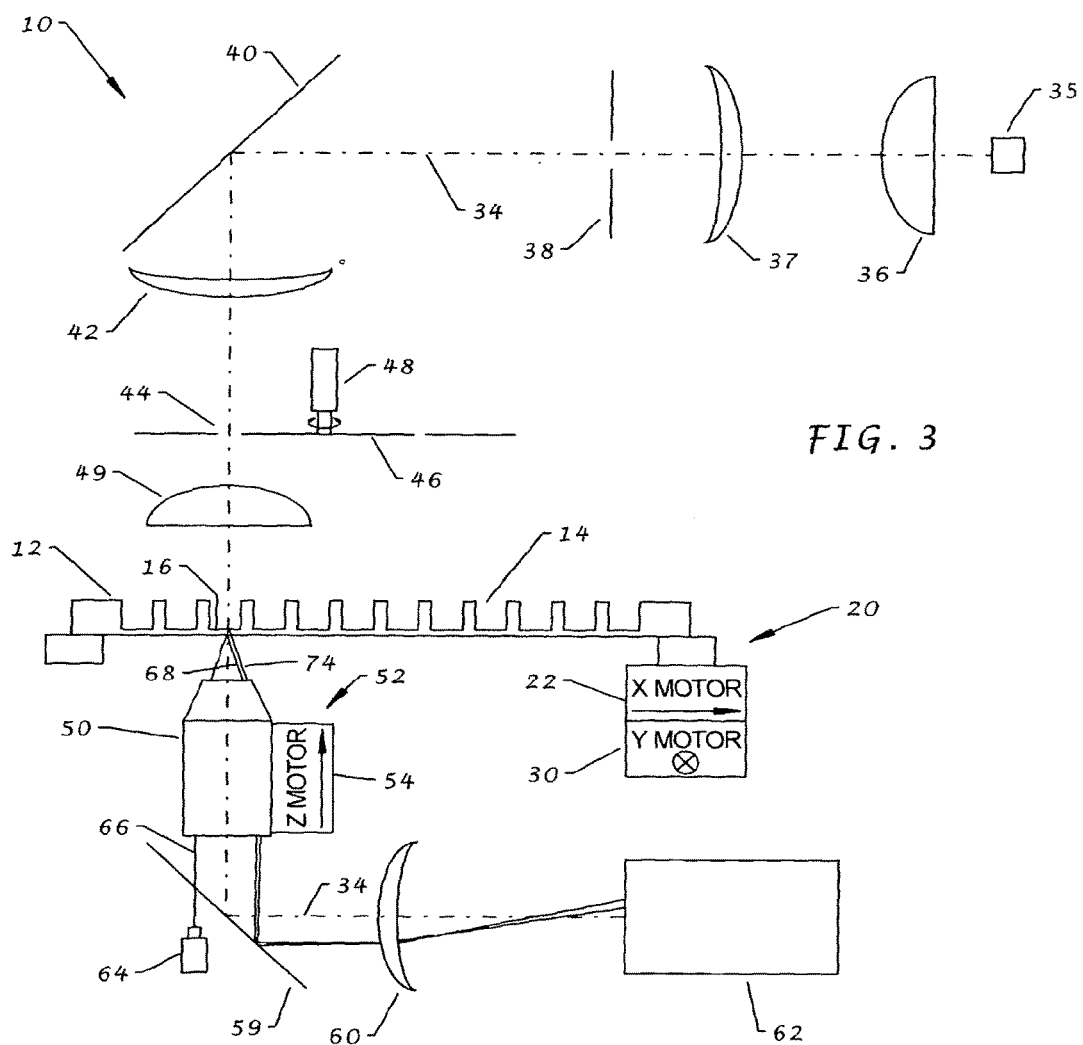
FIG. 3 is a diagram of optical components of an analysis apparatus embodying the invention.

Referring in particular to FIGS. 3 and 4, the apparatus 10 includes an XY stage 20 on which the microwell container 12 can be mounted. The XY stage 20 includes a X motor 22 and associated encoder 24 and feedback circuit 26 which can be controlled by a computer 28 to move the container 12 in the X direction, i.e. to the left and right as seen in FIG. 3. The XY stage 20 also includes a Y motor 30 and associated encoder 32 and feedback circuit 33 which can be controlled by the computer 28 to move the container 12 in the Y direction, i.e. in and out of the paper as seen in FIG. 3. The apparatus furthermore includes an optical system for illuminating a portion of the container and acquiring images of the illuminated portion. Specifically, the optical system includes, in order along an optical axis 34 above the container 12: a light source 35 which may be implemented by an LED; a collecting lens 36; a collimating lens 37; an aperture 38 which may be adjustable; a mirror 40; a focusing lens 42; an aperture 44 which may be a fixed aperture or may be one of several apertures provided in a wheel 46 or strip movable by a motor 48 to select a particular aperture; and a condenser lens 49 which projects the light from the source 35 onto the biological sample in the microwell container 12. The optical system furthermore includes, in order along an optical axis 34 below the container: an objective lens 50 which is mounted on a mechanical slide 52 including a motor 54 and associated encoder 56 and feedback circuit 58 which can be controlled by the computer 28 to move the objective lens 50 in the Z direction, i.e. up and down as seen in FIG. 3; a beam splitter 59 which may be implemented by a half-silvered mirror; a focusing lens 60; and a digital monochrome or color camera 62.

In addition to being able to illuminate the sample and acquire images thereof, the optical system is also arranged to enable a determination to be made of the height of the portion of the floor 16 of the container 12 which is currently in the view of the camera 62 so that the focus of the image acquired by the camera 62 can be appropriately set. Specifically, a laser source 64 is disposed behind the beam splitter 59 and projects a laser beam 66 through the beam splitter 59 and the objective lens 50 so that it impinges at an inclined angle on the container 12 adjacent the optical axis 34. A first reflected beam 68 is produced at the underside of the container 12 and is reflected back through the objective lens 50 and passes into the camera 62 where, as shown in FIG. 5, is produces a first spot 70 in the image 72 acquired by the camera 62. Also, in the regions of the compartments 14 of the container 12, a second reflected beam 74 is produced at top side of the floor of the container 12 and is reflected back through the objective lens 50 and passes into the camera 62 where, as shown in FIG. 5, is produces a second spot 76 in the image 72 acquired by the camera 62.

The computer 28 has a user interface 78 including, for example, a monitor, keyboard and mouse, and can produce an output 80, for example, to the monitor and/or to a printer and/or network connection.

The computer 28 is programmed to cause the apparatus 10 of FIGS. 3 and 4 to function in the manner that will now be described with reference to the flow diagram of FIG. 6A and its subroutines shown in the flow diagrams of FIGS. 6B-D.

Figure 6A:
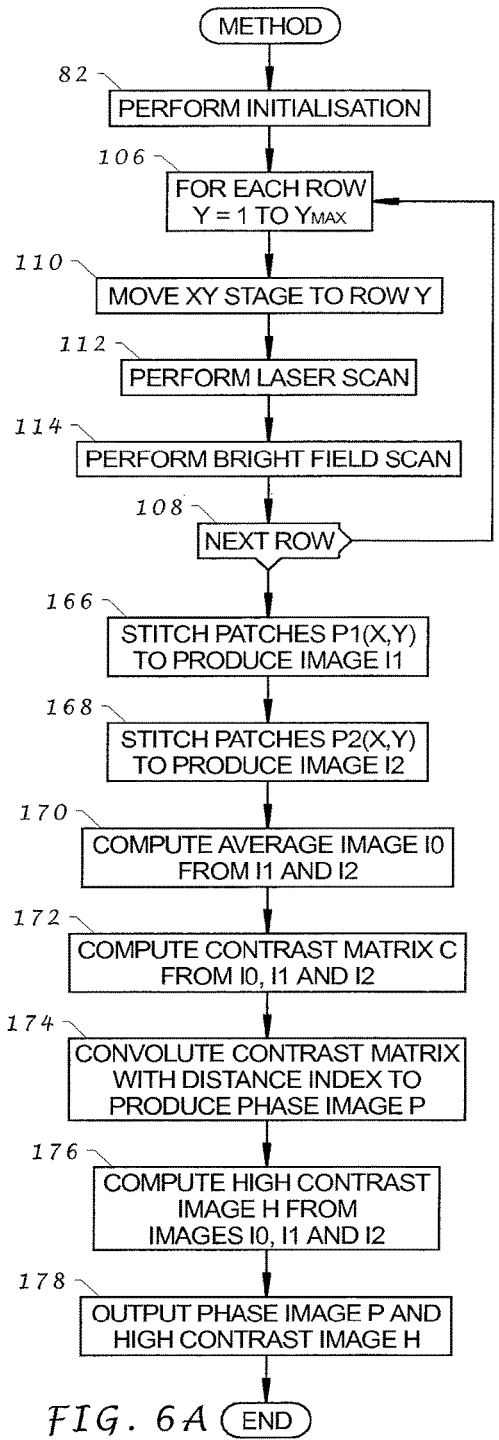
Figure 6B:
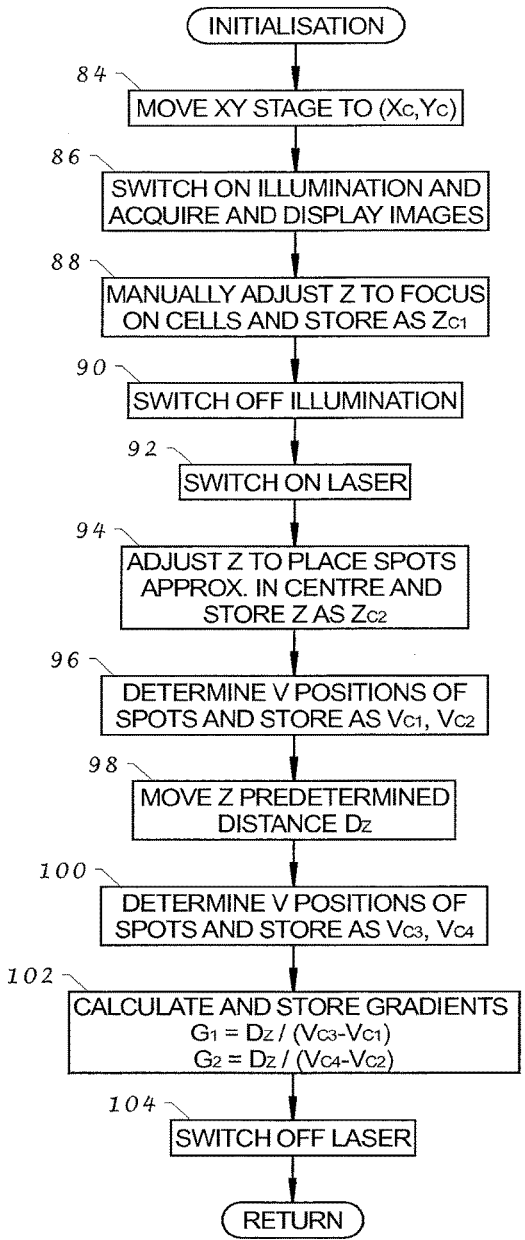

The first step 82 in the method of FIG. 6A is to perform an initialization routine as shown in FIG. 6B. In the initialization routine 82, the motors 22,30 are operated in step 84 to move the XY stage to a predetermined position $(X_c,Y_c)$ where one of the compartments 14 of the container 12 is centered on the optical axis 34. The light source 35 is then switched on in step 86 and the Z motor 54 is moved through a range of positions. An image is acquired by the camera 62 at each position and displayed on the user interface 78. It will be appreciated that the images have different focal planes. The user is then instructed by the user interface 78 to use the user interface 78 to select (for example using up and down arrows on the keyboard of the user interface 78) that one of the images for which the focal plane of the image approximately bisects the height of the cell or cells visible in the displayed image. At this position, the image has a focal height $F_0$ above the upper surface of the floor 16 of the container 12 at the position $(X_c,Y_c)$. Thereupon, in step 88, the Z position at which the objective lens 50 was set when the selected image was acquired is stored by the computer 28 as $Z_{c1}$ and in step 90 the light source 35 is switched off. The laser source 64 is then turned on in step 92, and in step 94 the Z position of the objective lens 50 is adjusted so that the brighter spot 70 of the two spots in the camera image 72 is approximately in the center of image. This may be done manually by the user through the user interface 78. Alternatively, the computer 28 may be programmed to use image recognition techniques to perform this step. The Z position of the objective lens 50 is stored as $Z_{c2}$. Then, in step 96 the computer 28 determines, using image recognition techniques, the positions $V_{c1},V_{c2}$ of the centers of two spots 70,76 in the image 72, and stores those two positions. The optical system is preferably arranged so that movement of the objective lens 50 in the Z direction produces movement of the spots 70, 76 parallel to one of the axes V in the coordinate system (U,V) used for the image 72. In step 98, the computer 28 causes the objective lens 50 to move a predetermined distance $\Delta_z$ (to a position $Z_{c2}+\Delta_z$). Then, in step 100 the computer 28 determines the new positions $V_{c3},V_{c4}$ of the centers of two spots 70, 76 in the image 72, and stores those two positions. It will be appreciated that the changes in the V positions of the two spots 70,76 are linearly related to the change in the Z position of the objective lens 50, and in step 102, the computer 28 calculates the gradients $G_1,G_2$ such that $G_1=\Delta z/(V_{c3}-V_{c1})$ and $G2=\Delta z/(V_{c4}-V_{c2})$, and stores the gradients $G_1,G_2$. In step 104, the laser source 64 is turned off, and the initialisation subroutine returns to the main routine of FIG. 6A.

The camera 62 captures an image of only a small portion of the container 12 and its contents with each operation of the camera 62. These small images portions will be referred to as 'patches.' In order to produce an image of the whole container 12 and its contents, a rectangular array of rows and columns of patches is acquired, and the patches are subsequently stitched together. The patches in a particular row are acquired with the same Y position of the XY stage, and for simplicity the Y positions will be taken to be integer numbers between and including 1 and $Y_{MAX}$. Similarly, the patches in a particular column are acquired with the same X position of the XY stage, and for simplicity the X positions will be taken to be integer numbers between and including 1 and $X_{MAX}$.

The aim is to acquire a pair of patches $P_1(X,Y)$, $P_2(X,Y)$ for each (X,Y) position, with each first patch $P_1(X, Y)$ having a first focal height relative to the upper surface of the floor 16 at that (X,Y) position, and with each second patch $P_2(X, Y)$ having a second focal height relative to the upper surface of the floor 16 at that (X,Y) position. However, if the height of the upper surface of the floor 16 cannot be ascertained at a particular (X,Y) position (for example because of the presence of a dividing wall 18 between adjacent compartments 14), the focal heights are determined relative to the lower surface of the floor 16 at that (X, Y) position. As mentioned above, the upper and lower surfaces of the floor 16 of the container 12 are not necessarily planar.

In order to achieve the above aim, for each row of patches from Y=1 to Y=$Y_{MAX}$, the apparatus 10 firstly scans the row in order to determine the focusing that should be employed for each patch in that row, and then scans the row again in order to acquire the patches. Therefore, referring again to FIG. 6A, there is a 'for each' loop 106,108, in which the XY stage 20 is moved to the appropriate row Y in step 110, and then a laser scan subroutine is performed in step 112, followed by a 'bright field scan' subroutine in step 114.

Figure 6C:
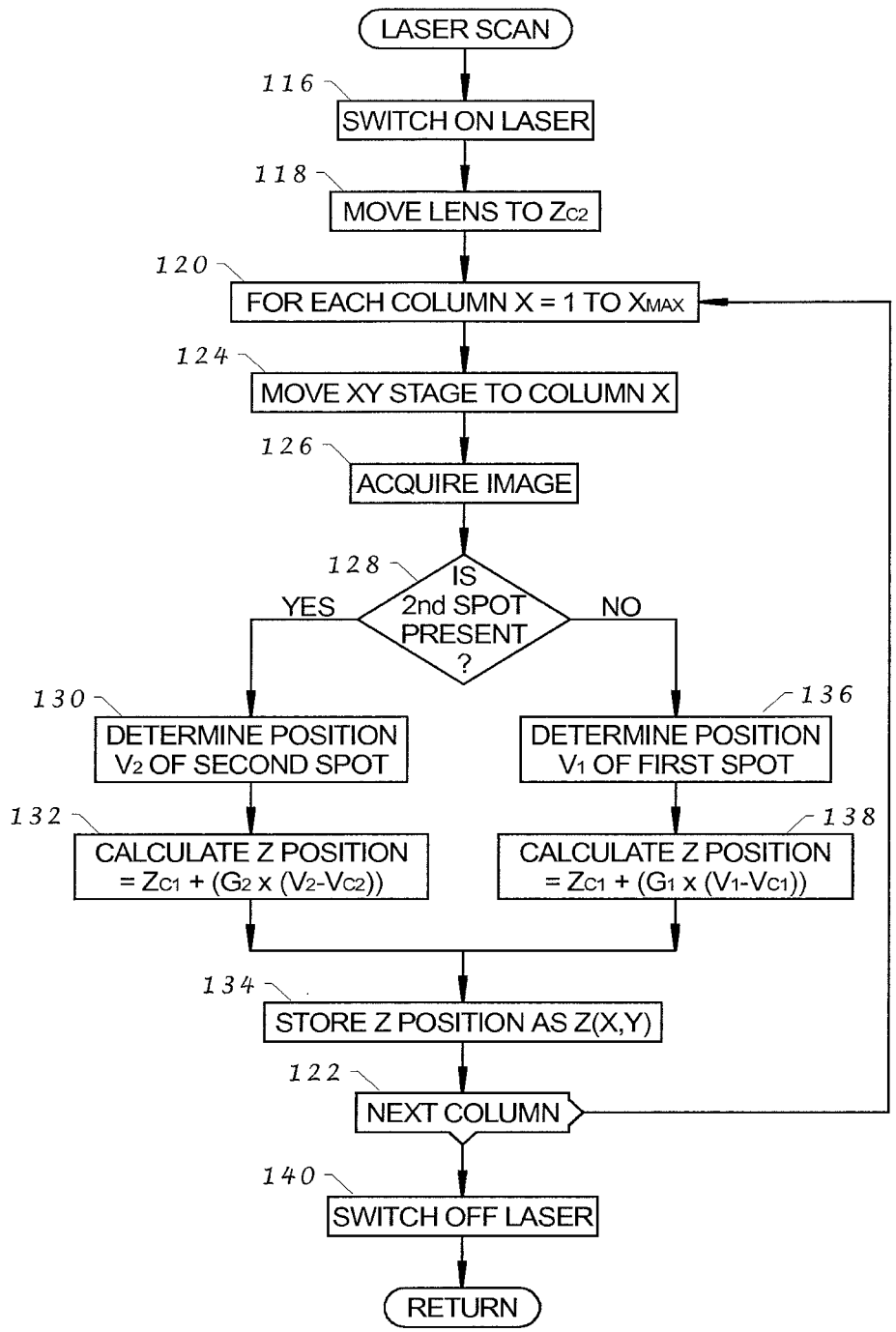
Figure 6D:
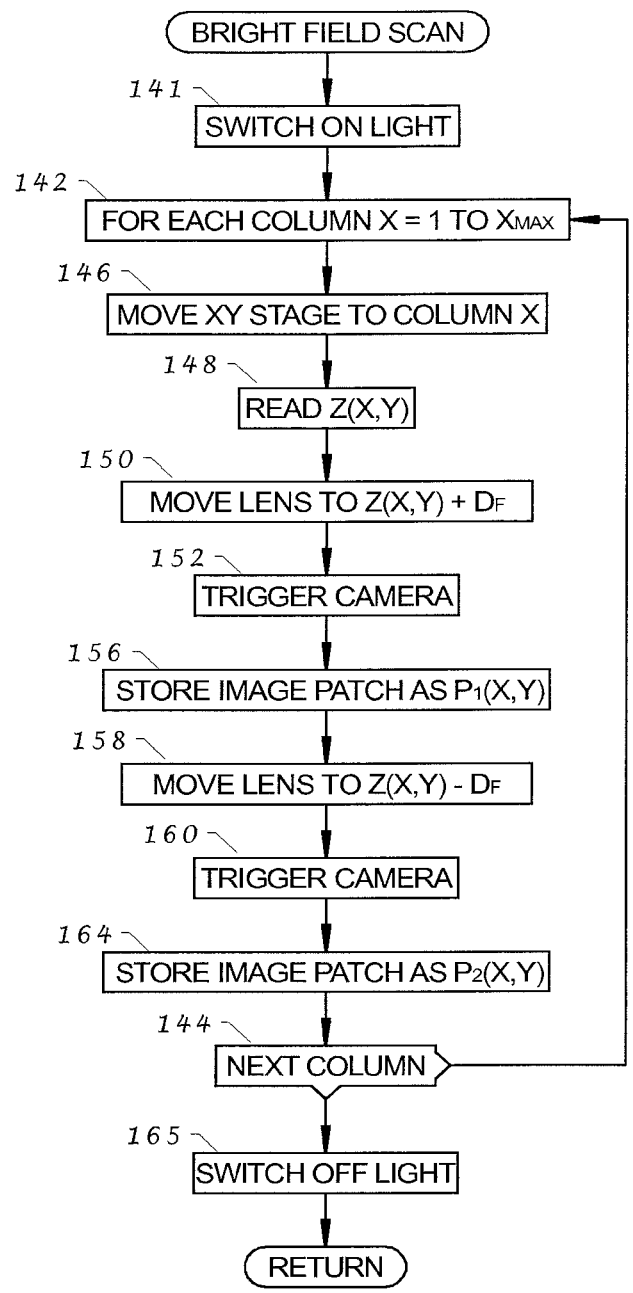

After the XY stage 20 has been moved to the appropriate row in step 110, then as shown in FIG. 6C, the laser source 64 is switched on in step 116, and in step 118 the objective lens is moved to the previously stored Z position Zc2. A 'for each' loop is then performed between steps 120 and 122 for each column from X=1 to X=$X_{MAX}$. In the 'for each' loop 120,122, the XY stage 20 is moved to the appropriate column X in step 124, and an image is acquired by the camera 62 in step 126. The image will be similar to the image 72 of FIG. 5, except that (a) the positions $V_1,V_2$ of the two spots 70,76 may be different to the positions $V_{c1},V_{c2}$ shown in FIG. 5, and (b) the second spot 76 may not be evident, for example because it is not present or because it is overlapped by the first spot 70. In step 128, the computer 28 employs image recognition techniques to determine whether a second spot is evident in the acquired image. If so, then in step 130 the computer 28 determines the position $V_2$ of the center of the second spot, and in step 132 calculates a Z position of the objective lens 50 to be used at the position (X,Y) from Z(X,Y)=$Z_{c1}$+($G_2$x($V_2$-$V_{c2}$)). The position Z(X, Y) is then stored in memory in step 134. On the other hand, if it is determined in step 128 that a second spot is not present in the image, then in step 136 the computer 28 determines the position V1 of the center of the first spot, and in step 138 calculates a Z position of the objective lens 50 to be used at the position (X,Y) from Z(X,Y)=Zc1+(G1x (V1−Vc1)). The position Z(X,Y) is then stored in memory in step 134. After the 'for each' loop has been completed for each column from X=1 to X=$X_{MAX}$, in step 140 the laser source 64 is switched off, and the laser scan subroutine is complete.

As mentioned above, after a laser scan has been performed for each row Y in step 112 of FIG. 6A, a bright field scan is performed for that row in step 114 of FIG. 6A. As shown in FIG. 6D, in each bright field scan 114, the light source 35 is switched on in step 141, and then a 'for each' loop is performed between steps 142,144 for each column for X=1 to X=$X_{MAX}$. In step 146, the XY stage 20 is moved to the appropriate column X. It should be noted that the XY stage is already positioned for the appropriate row Y. In step 148, the previously stored position Z(X,Y) for that (X,Y) position is read from memory, and in step 150 the computer 28 then causes the Z slide 52 to move the objective lens 50 to a position Z(X, Y)+Δf offset in one direction from the position Z(X,Y) by a predetermined amount Δf. In step 152, the camera 62 is triggered to commence an acquisition cycle. As a result, the camera 62 acquires an image patch $P_1$(X,Y), and in step 156 the computer 28 stores that image patch $P_1$(X,Y). In step 158 the computer 28 causes the Z slide 52 to move the objective lens 50 to a position Z(X,Y)+Δf offset in the opposite direction from the position Z(X,Y) by the predetermined amount Δf. In step 160, the camera 62 is triggered to commence an acquisition cycle. As a result, the camera 62 also acquires an image patch $P_2$(X,Y), and in step 164 the computer 28 stores that image patch $P_2$(X, Y). After the 'for each' loop has been performed for each column X, the light source 35 is switched off in step 165 at the end of the subroutine.

It will be appreciated from the above that, if the positions Z(X,Y) are calculated based on the positions of the second laser spot (in step 132), the patches $P_1$(X,Y) are captured with a first focal height $F_1$=Fo+Δf above the upper surface of the floor 16 of the container 12 at the position (X,Y) and the patches $P_2$(X,Y) are captured with a first focal height $F_2$=$F_0$−Δf above the upper surface of the floor 16 of the container 12 at the position (X,Y), despite variations in the height of the upper surface of the floor 16 of the container 12. If the positions Z(X,Y) are calculated based on the positions of the first laser spot (in step 138), the same holds true, provided that the thickness of the floor 16 of the container 12 is uniform.

Referring back to FIG. 6A, once the patches have been acquired, the in step 16t the computer 28 stitches together the patches $P_1$(X,Y) using known image processing techniques to produce an image $I_1$ having a focal height $F_1$ above the upper surface of the floor 16 of the container 12, and in step 168 the computer 28 stitches together the patches $P_2$(X,Y) to produce an image $I_2$ having a focal height $F_2$ above the upper surface of the floor 16 of the container 12. In step 170, the computer calculates an average image $I_0$ from the images $I_1$ and $I_2$ such that the value of each pixel in the average image I0 is the arithmetic mean of the values of the corresponding pixels in the images $I_1$, $I_2$. In other words, $I_0$(m,n)=($I_1$(m,n)+$I_2$(m,n))/2. Then, in step 172, the computer 28 computes a contrast matrix C having the same size of as the images $I_1$ and $I_2$ such that the value of each element in the contrast matrix C is equal to the difference between the values of the corresponding pixel in the average image $I_0$. In other words, C(m,n)=($I_1$(m,n)−$I_2$(m,n))/$I_0$, or C(m,n)=2×($I_1$(m,n)−$I_2$(m,n))/($I_1$(m,n)+$I_2$(m,n)). Then, in step 174, the computer 28 performs a 2-D convolution of the contrast matrix C with the distance index N to produce a phase matrix φ such that $$\phi = -\frac{q \times \Delta D}{4\lambda \times \Delta f} \times (C \otimes N)$$

where q is the pixel size, ΔD is the depth of field for the optical system; λ is the typical wavelength of the optical system. For example, in a system having a pixel size q of 2 µm, a depth of field ΔD of 12.8 µm, a focal height offset Δf of 12.8 µm and a typical wavelength λ of 550 nm, the phase image is given by φ≈−2×(C⊗N).

The distance index is a matrix having odd numbers of rows and columns. The number of elements in the distance index matrix is of the same order as the number of pixels occupied by a typical cell in the images $I_1$, $I_2$. In an example of the distance index matrix, the value of each of its elements, other than its center element, is inversely proportional to the distance between that element and the central element, and the value of the central element is zero. For example, a 5×5 distance index matrix N may be used as follows:

$$\begin{pmatrix} \sqrt{\frac{1}{8}} & \sqrt{\frac{1}{5}} & \frac{1}{2} & \sqrt{\frac{1}{5}} & \sqrt{\frac{1}{8}} \\ \sqrt{\frac{1}{5}} & \sqrt{\frac{1}{2}} & 1 & \sqrt{\frac{1}{2}} & \sqrt{\frac{1}{5}} \\ \frac{1}{2} & 1 & 0 & 1 & \frac{1}{2} \\ \sqrt{\frac{1}{5}} & \sqrt{\frac{1}{2}} & 1 & \sqrt{\frac{1}{2}} & \sqrt{\frac{1}{5}} \\ \sqrt{\frac{1}{8}} & \sqrt{\frac{1}{5}} & \frac{1}{2} & \sqrt{\frac{1}{5}} & \sqrt{\frac{1}{8}} \end{pmatrix}$$

The technique of 2-D convolution of matrices is well-known to those skilled in the art of image processing. For further information, reference is directed to John C. Russ, "The Image Processing Handbook", ISBN 978-1-4398-4045-0.

The phase matrix φ illustrates the phase change in the light as it passes through the container 12 and therefore illustrates the thickness of the cells in the sample in the container 12.

In addition to producing the phase matrix φ, in step 178 the computer 28 also computes a high contrast image H, which is easy for the human eye to interpret. Each pixel H(X, Y) in the high contrast image H is given by H(X,Y)=$I_0$+{A.[$I_1$(X,Y)−$I_2$(X,Y)]/2}, where A is an arbitrary coefficient.

The phase image φ and the high contrast H may be output from the system in step 178 and/or they may be further processed by the computer 28 is any desired manner.

Referring to FIG. 7, the timing diagram 180 at the top of that drawing shows the Y position of the XY stage 20 during the acquisition of one complete set of patches. The remaining timing diagrams in that drawing show the values of various parameters during the bright field scan phase of the process for a Y position of the XY stage 20 of Y=4. As can be seen, the X position of the XY stage 20 is incremented from X=1 to X=$X_{MAX}$. For each X position, the Z slide 52 is moved between its position for acquiring a patch $P_1(X,4)$ with a focal height of F1=$F_0$+Δf above the upper surface of the floor 16 of the container and its position for acquiring a patch $P_2(X,4)$ with a focal height of F2=Fo−Δf above the upper surface of the floor 16. It should be noted that Z positions for the patches $P_1(X,4)$ are not necessarily identical due to possible curvature of the floor of the container 12. Similarly, the Z positions for the patches $P_2(X,4)$ are not necessarily identical.

FIGS. 8A-B illustrate the arrangement of the patches $P_1(X,Y)$ in the image $I_1$ and of the patches $P_2(X, Y)$ in the image $I_2$. As can be seen in the example given, the patches in each image abut each other without overlapping.

Many modifications and developments may be made to the apparatus and method described above. For example, FIG. 9 shows a modification where the XY stage 20 is moved smoothly in the X direction during the bright field scan phase for each Y position, instead of its X position being incremented in steps. In view of this and as shown in FIGS. 10A-B, the patches $P_2$ of the image $I_2$ are offset by half a patch in the X direction from the patches $P_1$ of the image $I_1$. Because of the movement of the container 12 relative to the optical system during image acquisition, the camera acquisition period must be very short. This may be achieved by operating the light source 35 as a strobe light, rather than illuminating the container 12 and sample continuously during the bright field scan 114. The strobe light source 35 and camera 62 are preferably triggered by a common trigger signal as shown in the timing diagram 182 in FIG. 9, with the trigger pulses 184 being provided in pairs. The first pulse of each pair causes the camera 62 to commence an acquisition cycle and also causes a strobe flash of the light source 35. However, the response time of the camera 62 is not sufficiently fast for the camera 62 to have commenced integrating by the time the first flash has ended and so it is a wasted flash. The second trigger pulse of each pair is generated when the XY stage 20 has attained the appropriate X position, and while the camera 62 is part way through its acquisition cycle. Because of this, the camera 62 does not respond to the second trigger pulse of each pair. However, the second trigger pulse causes a second strobe flash of the light source 35 to illuminate the container 12 and sample in it so that a patch can be imaged. The XY stage 20 may also be moved smoothly in the X direction during the laser scan phase for each Y position. This modification may provide the advantages of increased speed of image acquisition and less wear on the XY stage 20.

Also, FIGS. 10A-B show a modification where the patches in each image overlap their neighboring patches slightly. During subsequent stitching together of the patches, the pixel values may be blended together in the overlapping regions so as to improve the appearance of the resulting image.

The light source 35 described above may be a broad band white light source, or it may be a narrow band colored light source. However, if a monochrome camera 62 is employed, the patches and images will be grey scale. In a modification to the apparatus, the light source 35 may be replaced by two or more light sources having different colors, such as the primary colors red, green and blue. Each patch acquisition may then be replaced by a set of two or more patch acquisitions, with a different colored light source being used for each patch in a set. The patches of each color may then be stitched together to produce an image of that color, and the images of the different colors may then be combined to produce a color image. For example, if three 8-bit grey scale images are produced while the object is illuminated with red, green and blue light, respectively, having pixel values R(X, Y), G(X, Y) and B(X,Y), respectively, at pixel position (X,Y), then a 24-bit RGB color image may be produced so that its pixel value I(X,Y) at each pixel position is given by I(X,Y)=[$2^{16}$×R(X,Y)]+[$2^8$×G(X,Y)]+[B(X,Y)]. This technique may be employed for acquiring the images at different focal heights, e.g. $F_1$, $F_2$, relative to the floor of the container 12, which may then be used for example in the production of a high contrast image in color. Alternatively, the technique may be employed to acquire a single image at a single focal height relative to the floor of the container 12.

In the initialization routine shown in FIG. 6B, the spot movement gradients $G_1$, $G_2$ are determined in steps 92-102, after the Z position has been adjusted for the $F_0$ focal height in steps 84-90. In a modification, the steps 92-102 may be intermingled with the steps 84-90.

In the case where the camera 62 and optical system has a large enough field of view and sufficient resolution, each of the images $I_1$, $I_2$ may be acquired as a single image, rather than as an array of patches which are subsequently stitched together.

In addition to producing the two images $I_1$, $I_2$ having focal heights; offset by a distance Δf to either side of the central focal plane $F_0$, other pairs of images may be acquired with different offsets and processed in a similar way to that described above. The multiple phase matrices and high contrast matrices may then be averaged or otherwise filtered.

It should be noted that the embodiment of the invention has been described above purely by way of example and that many other modifications and developments may be made thereto within the scope of the present invention.

The invention claimed is:

1. A method of analysis of a sample of biological tissue cells disposed on a platform, the sample being a thin phase object and the platform being substantially transparent, the method comprising:
   notionally dividing the sample up into an array of portions;
   determining a measure of the height of the platform on which each portion of the sample is disposed; and
   acquiring from light passing through the platform and the sample, using an optical system including a camera and an objective optical element disposed between the camera and the platform, a set of image patches of the portions of the sample with the focal height of each image patch being adjusted in dependence upon the respective measure of the height of the platform;
   stitching the image patches together to form an image of the sample; and
   using the image to assess characteristics of the sample;
   wherein the measure of the height of the platform is determined by:
      projecting a beam of light into the objective optical element substantially parallel to and offset from the optical axis so that:
         the beam is projected from the objective optical element to the platform at an inclined angle to the platform so that the beam is reflected, and
         the reflected beam is projected back into the objective optical element so that the reflected beam is projected from the objective optical element to the camera;
      using the camera to acquire an image of the reflected beam; and detecting the position of the reflected beam in the image.

2. The method of claim 1, wherein:
the image patches for the image are of overlapping portions of the sample; and
in the step of stitching together the image patches, the image patches are blended together in the areas of overlap.

3. The method of claim 2, wherein the reflected beam is reflected by an under surface of the platform;
a second beam is reflected by an upper surface of the platform and is projected back into the objective optical element so that the second reflected beam is also projected from the objective optical element to the camera; and
choosing whether to determine the measure of the height of the platform on which each portion of the sample is disposed from the reflected beam or the second reflected beam.

4. The method of claim 1, wherein acquiring the image comprises:
illuminating the sample with light of a first color and while doing so acquiring a first monochrome image component of the sample;
subsequently illuminating the sample with light of a second different color and while doing so acquiring a second monochrome image component of the sample; and
combining the first and second image components to produce a color image.

5. The method of claim 4, and further comprising:
illuminating the sample with light of a third different color and while doing so acquiring a third monochrome image component of the sample; and
combining the third image components with the first and second image components to produce the color image.

6. The method of claim 1, and further comprising scanning the platform and the optical system relative to each other.

7. The method of claim 6, wherein acquiring the image patches is performed while the platform and the optical system are moving relative to each other.

8. The method of claim 1, wherein focal heights of the image patches are adjusted by moving the optical element.

9. An apparatus for analysis of a sample of biological tissue cells on a platform, the apparatus comprising:
an optical system including a camera and an objective optical element disposed between the camera and the platform, the optical system configured to:
notionally divide the sample up into an array of portions;
determine a measure of the height of the platform on which each portion of the sample is disposed; and
acquire from light passing through the platform and the sample a set of image patches of the portions of the sample with the focal height of each image patch being adjusted in dependence upon the respective measure of the height of the platform; and
a computer system configured to:
stitch the image patches together to form an image of the sample; and
use the image to assess characteristics of the sample.

10. The apparatus of claim 9, wherein the optical system is configured to measure the height of the platform by:
projecting a beam of light into the objective optical element substantially parallel to and offset from the optical axis so that:
the beam is projected from the objective optical element to the platform at an inclined angle to the platform so that the beam is reflected; and
the reflected beam is projected back into the objective optical element so that the reflected beam is projected from the objective optical element to the camera;
using the camera to acquire an image of the reflected beam; and
detecting the position of the reflected beam in the image.

11. The apparatus of claim 9, wherein the image patches for the image are of overlapping portions of the sample, and the computer system is configured to blend the image patches together in the areas of overlap.

12. The apparatus of claim 11, wherein the platform comprises an under surface to reflect the reflected beam, and an upper surface to reflect a second beam that is projected back into the objective optical element to also project the second beam from the objective optical element to the camera; and wherein the computer system is further configured to choose whether to determine the measure of the height of the platform on which each portion of the sample is disposed from the reflected beam or the second reflected beam.

13. The apparatus of claim 9, wherein the platform and the optical system are movable relative to each other.

14. The apparatus of claim 9, wherein the optical system further comprises:
a light source, a collecting lens, a collimating lens, a first aperture, a mirror, a first focusing lens, a second aperture, and a condenser lens aligned in order on an optical axis on a first side of the sample to project light from the source onto the sample, and a movable mechanical slide with the objective optical element mounted thereon, a beam splitter, a second focusing lens, and the camera aligned in order on the optical axis on a second side of the sample, the optical system configured to acquire the image of the sample from light passing through the platform and the sample.

15. A non-transitory computer readable medium containing program instructions for a computer in the analysis of a sample of biological tissue cells disposed on a platform, the sample being a thin phase object and the platform being substantially transparent, the program instructions for causing the computer to:
notionally divide the sample up into an array of portions;
determine a measure of the height of the platform on which each portion of the sample is disposed;
cause an optical system including a camera and an objective optical element disposed between the camera and the platform to acquire from light passing through the platform and the sample a set of image patches of the portions of the sample with the focal height of each image patch being adjusted in dependence upon the respective measure of the height of the platform;
stitch the image patches together to form an image of the sample; and
use the image to assess characteristics of the sample.

16. The non-transitory computer readable medium of claim 15, wherein the program instructions further cause the computer to:
cause the optical system to obtain the image patches for the image as overlapping portions of the sample; and
blend the image patches together in the areas of overlap during stitching.

17. The non-transitory computer readable medium of claim 15, wherein the program instructions further cause the computer to:
- cause the optical system to illuminate the sample with light of a first color and while doing so acquire a first monochrome image component of the sample;
- cause the optical system to subsequently illuminate the sample with light of a second different color and while doing so acquire a second monochrome image component of the sample; and
- combine the first and second image components to produce a color image.

18. The non-transitory computer readable medium of claim 17, wherein the program instructions further cause the computer to:
- cause the optical system to illuminate the sample with light of a third different color and while doing so acquire a third monochrome image component of the sample; and
- combine the third image components with the first and second image components to produce the color image.

19. The non-transitory computer readable medium of claim 15, wherein the program instructions further cause the computer to:
- cause the optical system to scan the platform and the optical system relative to each other.

20. The non-transitory computer readable medium of claim 19, wherein the program instructions further cause the computer to:
- cause the optical system to adjust focal heights of the image patches by moving the optical element.

* * * * *